United States Patent [19]

Nevin

[11] Patent Number: 4,673,353

[45] Date of Patent: Jun. 16, 1987

[54] APPARATUS FOR APPLYING A LIGHT-CURABLE DENTAL COMPOSITION

[76] Inventor: Donald M. Nevin, 3 Clearmeadow Ct., Woodbury, N.Y. 11797

[21] Appl. No.: 869,148

[22] Filed: May 30, 1986

[51] Int. Cl.$^4$ .............................................. A61C 5/04
[52] U.S. Cl. .................................... 433/90; 433/215; 433/229
[58] Field of Search ................... 433/229, 215, 80, 83, 433/87, 89, 90; 350/96.34, 96.1

[56] References Cited

U.S. PATENT DOCUMENTS

| Re. 31,868 | 4/1985 | Beasley et al. | 350/96.34 |
|---|---|---|---|
| 2,186,143 | 1/1940 | Neugass | 350/96.1 |
| 2,507,909 | 5/1950 | Kaysen | 350/272 |
| 3,735,492 | 5/1973 | Karter et al. | 433/90 |
| 4,445,858 | 5/1984 | Johnson | 433/229 |
| 4,505,543 | 3/1985 | Ueba et al. | 350/96.34 |

Primary Examiner—Robert Peshock
Attorney, Agent, or Firm—Nolte, Nolte and Hunter

[57] ABSTRACT

An apparatus which can be used for exposing a light-curable dental composition to a curing light to harden the composition while the composition is applied to teeth so that the exposure of dentists' or technicians' eyes to such light is minimized. The apparatus has an opaque cylindrical receptacle which is open at its top and bottom. The bottom opening allows the receptacle to pick up and discharge the dental composition. The working end of an elongated plunger, having a clear plastic core and an opaque surface coating, extends through the top opening of the receptacle, and the other end of the plunger is connected to a source of curing light. The working end of the plunger can irradiate the dental composition within the receptacle with the curing light and can also be moved within the receptacle to force the irradiated dental composition outward of the bottom opening in the receptacle onto a tooth.

9 Claims, 4 Drawing Figures

APPARATUS FOR APPLYING A LIGHT-CURABLE DENTAL COMPOSITION

BACKGROUND OF THE INVENTION

This invention relates to an apparatus which can be used by a dentist for applying a light-curable dental composition to a patient's teeth and simultaneously exposing the composition to light which will cure the composition. This invention particularly relates to an apparatus for filling a tooth cavity with a light-curable filling material while simultaneously exposing the filling material to light that will cure the material.

Apparatus, such as conventional amalgam carriers, are well known for filling dental cavities with controlled amounts of a hardenable filling material. Typically, such apparatus have included a cylinder that is open at the top and bottom and a plunger within the cylinder that can move from its top towards its bottom. The bottom of the cylinder has been adapted to pick up a predetermined amount of the filling material from a container in which the material has been prepared or stored and to hold the picked-up filling material while it is transferred from the container to a position adjacent the tooth cavity. The plunger has been adapted to force the filling material out of the bottom of the cylinder into the cavity in the tooth.

With a light-curable dental composition, it has generally been the practice to shine a light on the composition for a predetermined time after applying the composition to a tooth, so that the composition hardens and bonds with the tooth to form a suitable permanent part of the tooth. The curing light (e.g., blue) has had a predetermined specific wavelength which can effect rapid curing of the resins in the dental composition. The specific procedure used for exposing the dental composition to curing light has varied, however, depending upon the particular composition and the particular use thereof. For example, it has been the practice with certain compositions, used as filling materials for tooth cavities, to expose the compositions in the tooth cavities to predetermined amounts of curing light each time fresh quantities of the compositions have been inserted into the cavities.

However, conventional procedures for curing light-curable dental compositions have tended to endanger the eyes of dentists and dental technicians using such compositions on their patients' teeth. In this regard, the light used to cure such compositions has tended to shine into the dentists' or technicians' eyes or be reflected off of dental and instrument surfaces into their eyes. With repeated exposures to a curing light, the light has tended to irritate significantly the eyes of the dentists or technicians. Ways have been sought, therefore, for exposing such dental compositions to curing light in a manner such that the exposure of dentists' or technicians' eyes to curing light is minimized.

SUMMARY OF THE INVENTION

In accordance with this invention, an apparatus is provided which can be used for applying a light-curable dental composition to teeth while exposing the composition to a curing light so that the exposure of dentists' or technicians' eyes to the curing light is minimized. The apparatus comprises:

an opaque receptacle having an interior cavity which can hold the dental composition; the receptacle having first and second openings in opposite ends thereof communicating with the cavity; the first opening being adapted to allow the receptacle to pick up the dental composition and hold it within the cavity; and an elongated plunger having opposite ends; one end of the plunger being the working end which extends through the second opening in the receptacle into its cavity; the other end of the plunger being connected to a source of the curing light; the plunger being made of a clear material capable of transmitting light between its ends and the plunger being coated on its side surfaces, between its ends, with a substantially opaque coating which prevents light, transmitted between its ends, from being substantially visible between its ends; the working end of the plunger being adapted to be moved further into the cavity of the receptacle towards its first opening to urge dental composition within the cavity outwardly of the receptacle through its first opening and onto a tooth.

DETAILED DESCRIPTION OF THE PREFERRED EMBODIMENT

Figure 1:
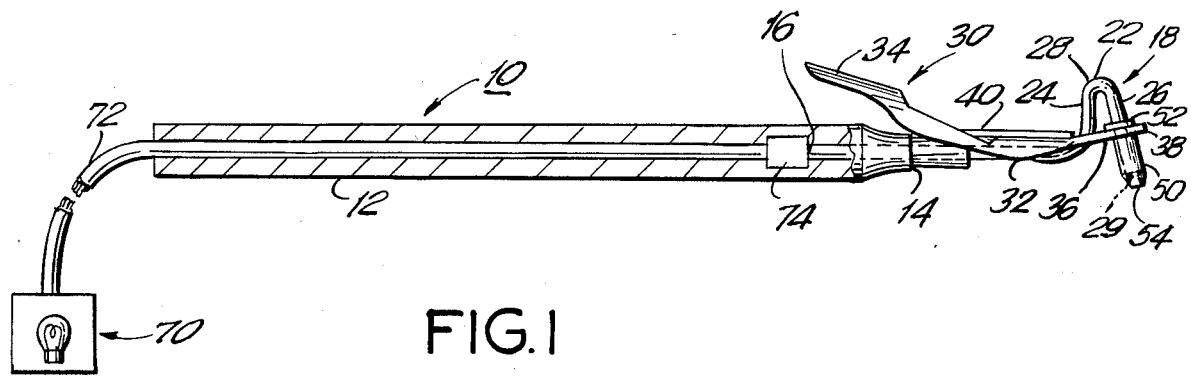
FIG. 1 is a schematic view of an apparatus in accordance with this invention which can be used to apply a light-curable dental composition to teeth while exposing the composition to curing light. The apparatus has an opaque cylindrical receptacle for picking up and holding small quantities of the dental composition and a plunger, one end of which is the working end that can be used for forcing the dental composition out of the receptacle and onto a tooth. The other end of the plunger is mounted within a handle of the apparatus and is connected to a source of curing light.

Shown in FIGS. 1–4 is an apparatus of this invention, generally 10, for (a) filling a tooth cavity with a light-curable material for repairing the tooth and (b) simultaneously exposing the material to light that will cure the material. The apparatus 10 includes an elongated, generally cylindrical, hollow, rigid handle 12. Inserted in one axial end 14 of the handle 12 is a proximal end 16 of a rigid elongated plunger 18 having a generally circular cross-section. The proximal end 16 of the plunger 18 is securely held within the one end 14 of the handle 12 so that the plunger cannot move horizontally or vertically relative to the handle. The remainder of the plunger 18, outside of the handle 12, extends distally away from the one end 14 of the handle 12 generally along the axis of the handle. In this regard, the plunger 18 has a generally straight portion 20 extending distally away from the one end 14 of the handle 12 along the axis of the handle 12. The distal end of the straight portion 20 of the plunger 18 is connected to a bent elbow 22 of the plunger that extends above the straight portion 20. The bent elbow 22 is formed by: an upwardly extending portion 24 connected at its bottom end to the straight portion 20; a downwardly extending portion 26; and a smoothly rounded, concave downward portion 28 connected to the top ends of the upwardly and downwardly extending portions 24 and 26. The bottom end of the downwardly extending portion 26 of the bent elbow 22 is the distal end 29 of the plunger 18, which is its working end as described below.

As shown in FIG. 1, a lever, generally 30, is pivotally connected at about its center 32 to the straight portion 20 of the plunger 18. One arm 34 of the lever 30 is located proximally above the one end 14 of the handle 12 and can be depressed toward the handle 12 by a finger of a dentist or technician holding the apparatus 10 by its handle 12. The other distal arm 36 of the lever 30 is located above, and extends generally parallel to, the straight portion 20 of the plunger 18. The distal lever arm 36 has an opening therein, adjacent its free distal end 38, through which the bent elbow 22 of the plunger 18 extends upwardly so that its rounded portion 28 is above the distal arm 36. The distal lever arm 36 can be elevated away from the straight portion 20 and the working end 29 of the plunger 18 and towards its rounded portion 28 by depressing the proximal lever arm 34.

Mounted on top of the one end 14 of the handle 12 is a spring 40 which extends distally away from the handle in a direction generally parallel to the handle's axis. The distal portions of the spring 40 rest on top of the center 32 of the lever 30 so as to hold the center 32 of the lever 30 on top of the straight portion 20 of the plunger 18, even when the proximal lever arm 34 is depressed to elevate the distal lever arm 36.

Mounted on the free end 38 of the distal lever arm 36 is a receptacle 50 having an internal cavity (not shown) which can be used for picking up and holding a light-curable dental composition to be applied to teeth. The receptacle 50 preferably has a generally cylindrical configuration with openings 52 and 54 at its top and bottom axial ends, respectively. The bottom opening 54 is adapted to be used for picking up the dental composition so that it can be held in the cavity of the receptacle until it is to be transferred to a tooth. The downwardly extending portion 26 of the bent elbow 22 of the plunger 18 extends downwardly through the top opening 52 in the receptacle 50 towards its bottom opening 54, so that the working end 29 of the plunger 18 is located within the cavity of the receptacle 50 above its bottom opening 54. A dental composition can be dispensed onto a tooth from the cavity of the receptacle 50 through its bottom opening 54 by simply depressing the proximal lever arm 34, thereby elevating the distal lever arm 36 and the receptacle 50 relative to the working end 29 of the plunger 18 so as to move the working end 29 of the plunger 18 axially within the receptacle 50 towards its bottom opening 54.

Thus, the apparatus 10 of this invention has a structure and operation, as described above, which are found in conventional amalgam carriers.

In accordance with this invention, the receptacle 50 is made from an inert metal or opaque plastic.

Figure 2:
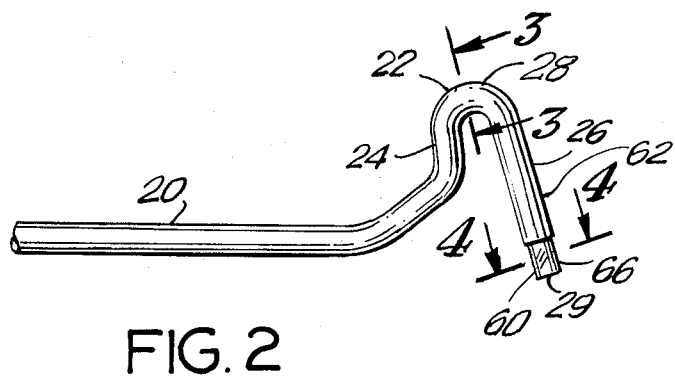
FIG. 2 is a detailed schematic view of portions of the plunger of the apparatus of FIG. 1 outside of the handle of the apparatus.
Figure 3:
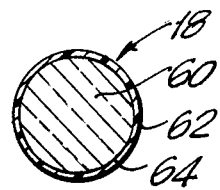
FIG. 3 is a sectional view of the plunger, taken along line 3—3 in FIG. 2, showing the clear core of the plunger with it opaque side surface coating.
Figure 4:
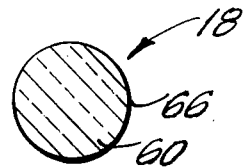
FIG. 4 is a sectional view of the plunger, taken along line 4—4 in FIG. 2, showing the clear core of the plunger without its side surface coating adjacent its working end.

Also in accordance with this invention, the plunger 18 is made from a clear rigid, preferably non-breakable, inert material which can efficiently transmit a curing light along the length of the plunger 18 between its opposite ends 16 and 29. The plunger can be made of any conventional clear plastic such as a methacrylic acid polymer, a methylmethacrylate polymer, a polycarbonate or a polystyrene. Preferably, the plunger 18 is formed by a clear solid inert plastic core 60 surrounded by an inert metal or opaque plastic coating 62. The opaque coating 62 covers the side surfaces, generally 64, of the plunger 18 between its ends 16 and 29 to prevent curing light, transmitted between the ends of the plunger, from being substantially visible between its ends. In this regard, it is preferred that, as shown in FIGS. 2–4, the coating 62 entirely cover the side surfaces 64 of plunger 18 outside of the opaque receptacle 50 but not cover portions 66 of the plunger side surfaces 64 which are adjacent to the distal working end 29 of the plunger and are never moved outwardly of the opaque receptacle 50 through its top opening 52 by the action of the lever 30 when applying a dental composition to teeth. Such uncoated side surfaces 66 provide a larger area at the working end 29 of the plunger 18 which can irradiate a dental composition in the cavity in the receptacle 50 with a curing light.

Also in accordance with this invention, the proximal end 16 of the plunger 18, mounted in the handle 12, is connected to a source of a curing light (e.g., blue light) 70. In this regard, the source of curing light 70 can be connected to the plunger 18 in any conventional manner but is preferably connected by means of a conventional bundle of optical fibers 72 and a conventional coupling 74 within the handle 12 that connects the fiber bundle 72 to the proximal end 16 of the plunger 18.

The apparatus 10 of this invention can be used for filling a tooth cavity with a light-curable filling material while simultaneously exposing the filling material to light that will cure the material. A small quantity of a filling material (not shown) can be urged upwardly into the cavity within the receptacle 50 on the distal end 38 of the distal lever arm 36 through the bottom opening 54 in the receptacle. This can be accomplished, for example, by pushing the bottom opening 54 of the receptacle 50 downwardly into the filling material within a container in which the filling material has been prepared or stored so that the material is forced upwardly into the cavity in the receptacle 50. Then, the small amount of filling material, so picked up by the receptacle 50, can be transferred within the receptacle to a position adjacent the tooth cavity, to be filled. Then, the proximal lever arm 34 can be depressed toward the handle 12 so that the distal lever arm 36, along with the receptacle 50 on the free end 38 of the distal lever arm 36, moves upwardly towards the rounded portion 28 of the bent elbow 22 of the plunger 18. Thereby, the working end 29 of the plunger 18 is moved downwardly within the receptacle 50, away from its top opening 52 and towards its bottom opening 54, which forces the filling material within the receptacle 50 outwardly of its bottom opening 54 into the tooth cavity. While the filling material is held within the receptacle 50 and while the working end 29 of the plunger 18 is thereafter forcing the filling material out of the receptacle 50, the filling material is irradiated by curing light that emanates from the working end 29 of the plunger and the uncoated side surfaces 66 adjacent the working end 29 and that comes from the light source 70 via the fiber bundle 72, the coupling 74 and the proximal end 16 of the plunger 18. In accordance with this invention, the opaque coating 62 on the side surfaces 64 of the plunger 18 and the opaque receptacle 50 substantially prevent the curing light from shining in the eyes of the dentist or technician, using the apparatus 10, which could cause irritation of the eyes while the filling material is being irradiated to cure it.

It is thought that this invention and many of its attendant advantages will be understood from the foregoing description, and it will be apparent that various changes and modifications can be made in the invention without departing from the spirit and scope thereof or sacrificing all of its material advantages, the apparatus 10 hereinbefore described being merely a preferred embodiment. In this regard, a switch (not shown) can be connected to the lever 30 and the light source 70 so that the light source transmits curing light to the working end 29 of the plunger 18 only when the proximal lever arm 34 is depressed. Also, terms such as "top", "bottom", "upwardly", "downwardly", "distal" and "proximal" are simply relative terms used to describe the apparatus 10 of this invention as shown in FIGS. 1-4. Furthermore, the apparatus 10 can be modified so that it can be used, for example, for shaping or otherwise manipulating a light-curable dental composition once the composition has been applied to a patient's teeth. In this regard, the lever 30 and the opaque receptacle 50 can, if desired, be eliminated from the apparatus 10, and the distal working end 29 of the plunger 18 can be suitably shaped so that the plunger can be used as a tool for shaping the light-curable composition on teeth, provided the opaque coating 62 entirely covers the plunger's side surfaces 64 between its ends 16 and 29.

I claim:

1. An apparatus for applying a light-curable dental composition to teeth while exposing the composition to a curing light, comprising:

an opaque receptacle having an interior cavity which can hold the dental composition; the receptacle having first and second openings in opposite ends thereof communicating with the cavity; the first opening being adapted to allow the receptacle to pick up the dental composition and hold it within the cavity; and an elongated plunger having opposite ends; one end of the plunger being the working end which extends through the second opening in the receptacle into its cavity; the other end of the plunger being connected to a source of the curing light; the plunger being made of a clear material capable of transmitting light between its ends and the plunger being coated on its side surfaces, between its ends, with a substantially opaque coating which prevents light, transmitted between its ends, from being substantially visible between its ends; the working end of the plunger being adapted to be moved further into the cavity of the receptacle towards its first opening to urge dental composition within the cavity outwardly of the receptacle through its first opening and onto a tooth.

2. The apparatus of claim 1, wherein the clear material of the plunger is a clear plastic.

3. The apparatus of claim 2, wherein the clear plastic is selected from the group consisting of a methacrylic acid polymer, a methylmethacrylate polymer, a polycarbonate and a polystyrene.

4. The apparatus of claim 1, wherein the opaque coating entirely covers the side surfaces of the plunger outside of the receptacle but does not cover the side surfaces of the plunger which are adjacent to the working end of the plunger and are never moved outwardly of the receptacle through its second opening when applying the dental composition.

5. The apparatus of claim 1, wherein an elongated handle is connected to the other end of the plunger that is connected to the source of light; and the working end of the plunger is an end of a downwardly extending portion of a concave downward, bent elbow in the plunger.

6. An apparatus for manipulating a light-curable dental composition while exposing the composition to a curing light, comprising:

an elongated rigid member having opposite ends; one end of the rigid member being the working end of the apparatus and the other end of the rigid member being connected to a source of the curing light; the rigid member being made of a clear material capable of transmitting light between its ends and being coated on its side surfaces, between its ends, with a substantially opaque coating which prevents light, transmitted between its ends, from being substantially visible between its ends; the working end of the rigid member being adapted to be used for manipulating the dental composition while exposing the dental composition to the curing light.

7. The apparatus of claim 6, wherein the clear material of the rigid member is a clear plastic.

8. The apparatus of claim 7, wherein the clear plastic is selected from the group consisting of a methacrylic acid polymer, a methylmethacrylate polymer, a polycarbonate and a polystyrene.

9. The apparatus of claim 6, wherein the opaque coating entirely covers the side surfaces of the rigid member.

* * * * *